(12) United States Patent
Todd et al.

(10) Patent No.: US 9,687,313 B2
(45) Date of Patent: Jun. 27, 2017

(54) PACKAGE FOR OSTOMY BARRIER RING

(71) Applicant: Hollister Incorporated, Libertyville, IL (US)

(72) Inventors: Russell J. Todd, Highland Park, IL (US); Cale N. Street, Grayslake, IL (US); Dion A. Jackson, Chicago, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 14/911,640

(22) PCT Filed: Oct. 20, 2014

(86) PCT No.: PCT/US2014/061362
§ 371 (c)(1),
(2) Date: Feb. 11, 2016

(87) PCT Pub. No.: WO2015/102735
PCT Pub. Date: Jul. 9, 2015

(65) Prior Publication Data
US 2016/0193003 A1 Jul. 7, 2016

Related U.S. Application Data

(60) Provisional application No. 61/921,922, filed on Dec. 30, 2013.

(51) Int. Cl.
*A61B 19/02* (2006.01)
*A61B 50/30* (2016.01)
(Continued)

(52) U.S. Cl.
CPC .............. *A61B 50/30* (2016.02); *A61F 5/445* (2013.01); *A61B 2050/005* (2016.02);
(Continued)

(58) Field of Classification Search
CPC ......... A61B 50/30; A61B 50/33; A61B 50/36; A61B 50/37; A61B 50/39;
(Continued)

(56) References Cited

U.S. PATENT DOCUMENTS 3,710,975 A * 1/1973 Jansen ................ B65D 43/162
206/456
5,220,999 A 6/1993 Goulette
(Continued)

FOREIGN PATENT DOCUMENTS

BE 1007377 A7 5/1995
WO 2013014231 A1 1/2013

*Primary Examiner* — Steven A. Reynolds
*Assistant Examiner* — Javier A Pagan
(74) *Attorney, Agent, or Firm* — Levenfeld Pearlstein, LLC (57) ABSTRACT

A package for an ostomy barrier ring is provided. The package includes a first shell, a second shell and a hinge connecting the first and second shells. The first shell includes a first stacking wall having a first interior side and a first exterior side, a first nesting structure formed on the first stacking wall, and a first sidewall extending from and about the first stacking wall. The second shell includes a second stacking wall having a second interior side and a second exterior side, a second nesting structure formed on the second stacking wall, and a second sidewall extending from and about the second stacking wall. The hinge allows the first shell and second shell to rotate relative to one another. A plurality of packages may be stacked with the first nesting structure of one package received in the second nesting structure of an adjacent package.

16 Claims, 5 Drawing Sheets

(51) Int. Cl.
*A61F 5/445* (2006.01)
*A61B 50/00* (2016.01)
(52) U.S. Cl.
CPC .............. *A61B 2050/0056* (2016.02); *A61B 2050/3006* (2016.02); *A61B 2050/3007* (2016.02)
(58) Field of Classification Search
CPC .... A61B 2050/3006; A61B 2050/3007; A61B 2050/3009
See application file for complete search history.

(56) References Cited

U.S. PATENT DOCUMENTS

| | | | | |
|---|---|---|---|---|
| D452,628 S | * | 1/2002 | Stauffer | D6/407 |
| 2003/0057127 A1 | * | 3/2003 | Lambert | B65D 21/0213 206/581 |

* cited by examiner

PACKAGE FOR OSTOMY BARRIER RING

BACKGROUND

The following description relates to packaging for an ostomy barrier ring, and in particular, a stackable clamshell package for an ostomy barrier ring.

Ostomy barrier rings are typically circular in shape and include a central opening through which a stoma is positioned. Due to the replaceable nature of the barrier rings, multiple barrier rings are often provided in a single outer container, such as a cardboard box. Individual barrier rings may be provided in individual packages within the outer container.

Individual packages for barrier rings may be formed as plastic packages having a base and a lid hingedly secured to the base. The packages are often removed from the outer container and stored on a shelf, in a cabinet, or in a drawer. In some cases, the packages may be stacked on top of one another. However, if the stack is bumped or otherwise disturbed, it may topple.

Accordingly, is desirable to provide an ostomy barrier ring package having positive positioning features allowing similar packages to be stacked in a nesting relationship, so that the stack of packages can be neatly and orderly stacked and stored and may resist toppling if bumped or disturbed.

SUMMARY

According to one embodiment, there is provided a package for an ostomy barrier ring. The package includes a first shell having a first stacking wall having a first interior side and a first exterior side, a first nesting structure formed on the first stacking wall, and a first sidewall extending from and about the first stacking wall. The package further includes a second shell having a second stacking wall having a second interior side and a second exterior side, a second nesting structure formed on the second stacking wall, and a second sidewall extending from and about the second stacking wall. The package also includes a hinge connected to the first shell and second shell allowing the first shell and second shell to rotate relative to one another between an open position and closed position.

According to another embodiment there is provided a plurality of packages for ostomy barrier rings, each package including a first shell, a second shell and a hinge. The first shell includes a first stacking wall having a first interior side and a first exterior side, a first nesting structure formed on the first stacking wall, and a first sidewall extending from and about the first stacking wall. The second shell includes a second stacking wall having a second interior side and a second exterior side, a second nesting structure formed on the second stacking wall, and a second sidewall extending from and about the second stacking wall. The hinge is connected to the first shell and second shell allowing the first shell and second shell to rotate relative to one another between an open position and closed position. The second nesting structure of one package of the plurality of packages is configured to receive the first nesting structure of another package of the plurality of packages.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 1:
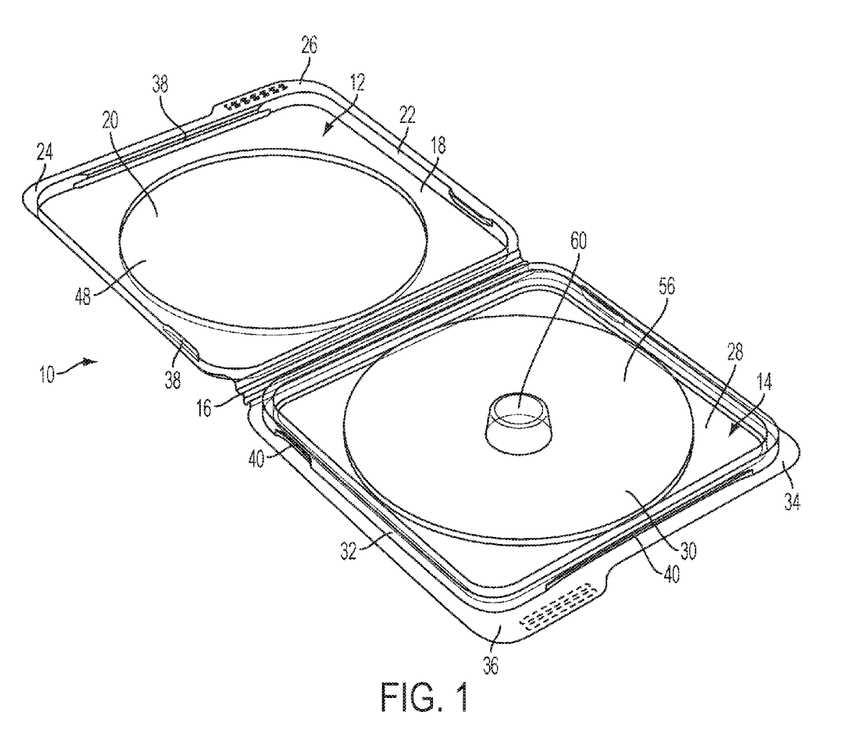
FIG. 1 is a perspective view of an ostomy barrier ring package in an open position according to an embodiment.
Figure 2:
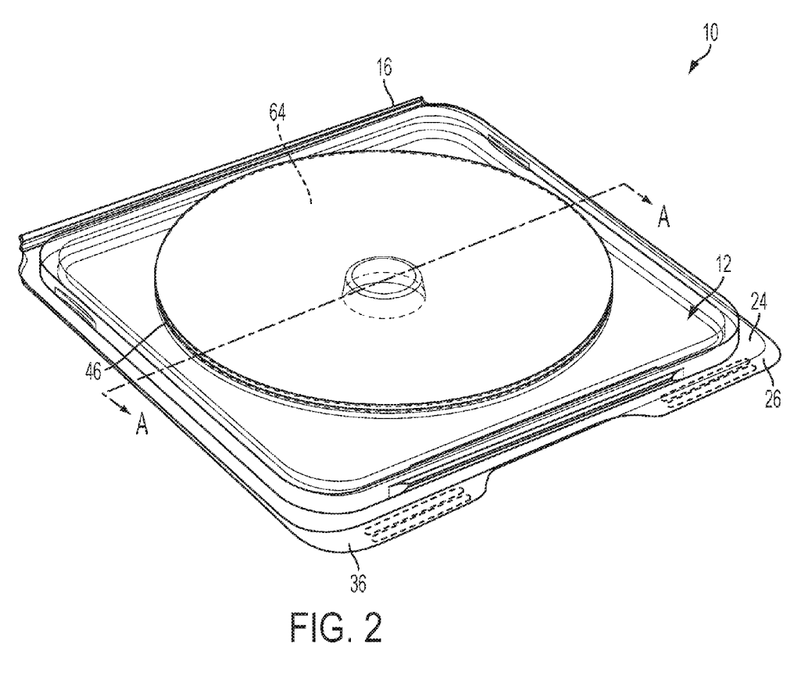
FIG. 2 is a perspective view of an ostomy barrier ring package in a closed position according to an embodiment.

FIG. 1 is a perspective view of an embodiment of a package 10 for an ostomy barrier ring in an open position. FIG. 2 is a perspective view of the package in a closed position. Referring to the examples in FIGS. 1 and 2, the package 10 includes a first shell 12, a second shell 14 and a hinge 16 connected between the first shell 12 and second shell 14. The hinge 16 pivotably connects the first shell 12 to the second shell 14 such that the first shell 12 and second shell 14 may rotate relative to one another between an open position (FIG. 1) and a closed position (FIG. 2).

The first shell 12 includes a first stacking wall 18 having a first nesting structure 20 formed thereon. The first shell 12 also includes a first sidewall 22 extending from the first stacking wall 18. In one embodiment, the first sidewall 22 extends from the first stacking wall 18 at approximately ninety degrees. However, it is understood that this angle may vary. The first sidewall 22 extends about a periphery of the first stacking wall 18.

The first shell 12 may also include a first peripheral flange 24 extending from the first sidewall 22. In one embodiment, the first peripheral flange 24 extends from the first sidewall 22 at approximately ninety degrees, but it is understood this angle may vary. The first peripheral flange 24 extends about at least a portion of the first sidewall 22. In some embodiments, the first peripheral flange 24 may extend completely about the periphery of the first sidewall 22. The hinge 16 may be connected to the first peripheral flange 24. Alternatively, the first peripheral flange 24 may extend about a portion of the periphery of the first sidewall 22, and the hinge 16 may be connected to the first sidewall 22.

The first peripheral flange 24 may also include at least one first opening tab 26. The first opening tab 26 may be formed as an area of extended width on the first peripheral flange 24. For example, the first opening tab 26 may be formed as a portion extending further out from the first sidewall 22 than adjacent portions of the first peripheral flange 24. A user may grasp the first opening tab 26, for example, to manipulate the first shell 12 when opening the package 10.

With further reference to FIGS. 1 and 2, the second shell 14 includes a second stacking wall 28 having a second nesting structure 30 formed thereon. The second shell 14 also includes a second sidewall 32 extending from the second stacking wall 28. In one embodiment, the second sidewall 32 extends from the second stacking wall 28 at approximately ninety degrees. However, it is understood that this angle may vary. The second sidewall 32 extends about a periphery of the second stacking wall 28.

The second shell 14 may also include a second peripheral flange 34 extending from the second sidewall 32. In one embodiment, the second peripheral flange 34 extends from the second sidewall 32 at approximately ninety degrees, but it is understood this angle may vary. The second peripheral flange 34 extends about at least a portion of the second sidewall 32. In some embodiments, the second peripheral flange 34 may extend completely about the periphery of the second sidewall 32. The hinge 16 may be connected to the second peripheral flange 34. Alternatively, the second peripheral flange 34 may extend about a portion of the periphery of the second sidewall 32, and the hinge 16 may be connected to the second sidewall 32.

The second peripheral flange 34 may also include at least one second opening tab 36. The second opening tab 36 may be formed as an area of extended width on the second peripheral flange 34. For example, the second opening tab 36 may be formed as a portion extending further out from the second sidewall 32 than adjacent portions of the second peripheral flange 34. A user may grasp the second opening tab 36, for example, to manipulate the second shell 14 when opening the package 10.

Still referring to FIGS. 1 and 2, when moving from the open position (FIG. 1) to the closed position (FIG. 2) one of the first sidewall 22 and the second sidewall 32 is configured to be received within the other of the first sidewall 22 and the second sidewall 32. For example, as shown in FIGS. 1 and 2, the second sidewall 32 may be received within the first sidewall 22 in the closed position.

One of the first sidewall 22 and the second sidewall 32 may include at least one lug 38, while the other of the first sidewall 22 and the second sidewall may include at least one corresponding groove 40. In the examples in FIGS. 1 and 2, the first sidewall 22 includes the at least one lug 38 while the second sidewall 32 includes the at least one corresponding groove 40. The corresponding groove 40 is configured to receive a respective lug 38 in an interference fit. Accordingly, in the examples shown in FIGS. 1 and 2, when rotating the first shell 12 relative to the second shell 14 to move the package 10 to the closed position, a lug 38 may come into contact with the second sidewall. This may cause an increase in resistance while rotating the first shell 12 and the second shell 14 relative to another. Continued movement of the first shell 12 and the second shell 14 relative to one another causes the lug 38 to be received in a respective groove 40. Accordingly, the package 10 may be "snapped" shut in the closed position due the interference between the lug 38 and groove 40.

The lug 38 and groove 40 are also configured to maintain the package 10 in the closed position. That is, an additional force or effort may be required by the user to remove the lug 38 from the groove 40. Accordingly, inadvertent or accidental opening of the package 10 may be avoided. The at least one lug 38 may be moved into and removed from respective at least one grooves 40 as a result of elastic deformation at the first shell 12 and second shell 14.

Figure 3:
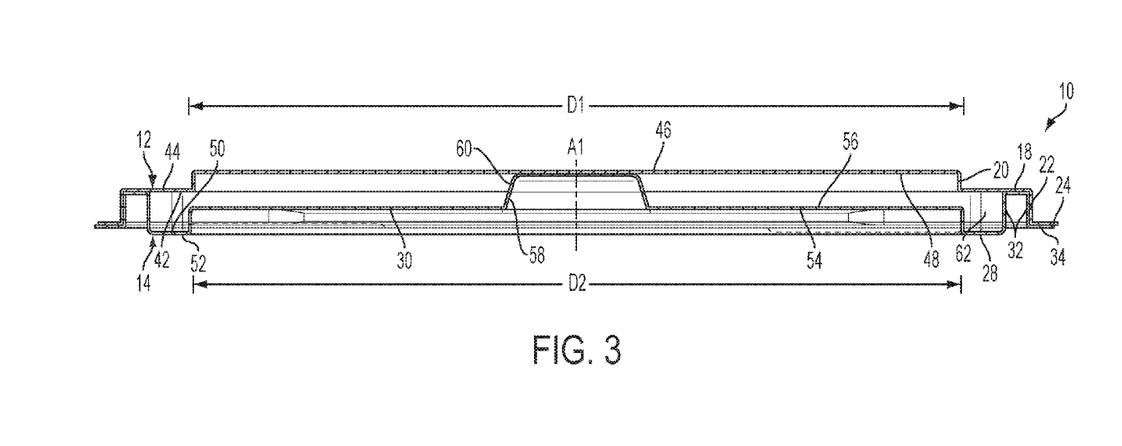
FIG. 3 is a front cross-sectional view of the ostomy barrier ring package of FIG. 2 taken at A-A, according to an embodiment.

FIG. 3 is a cross-section of the package 10 in the closed position, taken at A-A in FIG. 2. Referring to the example in FIG. 3, the first stacking wall 18 of the first shell 12 includes a first interior side 42 and a first exterior side 44. In one embodiment, the first nesting structure 20 may include a plateau 46 extending outwardly from the first exterior side 44. The plateau 46 defines a corresponding first recess 48 on the first interior side 42 of the first stacking wall 18.

In one embodiment, for example, as shown in FIGS. 1 and 2, the plateau 46, and in turn, the first recess 48, may formed in a substantially circular shape having a first diameter D1.

It is understood, however, that the plateau 46 and corresponding first recess 48 may be formed in other shapes. For example, the plateau 46 and first recess 48 may be formed substantially as a square, rectangle, triangle, oval or the like. In addition, more than one plateau 46 and first recess 48 may be formed on the first stacking wall 18.

Still referring to the example in FIG. 3, the second stacking wall 28 of the second shell 14 includes a second interior side 50 and a second exterior side 52. In one embodiment, the second nesting structure 30 may include a second recess 54 extending inwardly from the second exterior side 52. The second recess 54 defines a corresponding pedestal 56 on the second interior side 50 of the second stacking wall 28.

A third recess 58 may be positioned in, and extend from the second recess 54 at the second exterior side 52. The third recess 58 defines a corresponding projection 60 extending from the pedestal 56 at the second interior side 50. In one embodiment, the projection 60 extends from the pedestal 56 at the second interior side 50 to a position beyond an extent of the second sidewall 32. That is, in one embodiment, a combined height of the projection 60 and pedestal 56 above the second stacking wall 28 exceeds a height of the second sidewall 32 above the second stacking wall 28. The projection 60 may extend into the first recess 48 when the package 10 is in the closed position.

In one embodiment, for example, as shown in FIGS. 1 and 2, the second recess 54 may formed in a substantially the same shape as the plateau 46. That is, the second recess 54 may be formed in substantially circular shape and have a second diameter D2. It is understood, however, that the second recess 54, and in turn, the pedestal 56, may be formed in other shapes. For example, the second recess 54 and pedestal 56 may be formed substantially as a square, rectangle, triangle, oval or the like. In addition, more than one second recess 54 may be formed on the second stacking wall 28.

Figure 4:
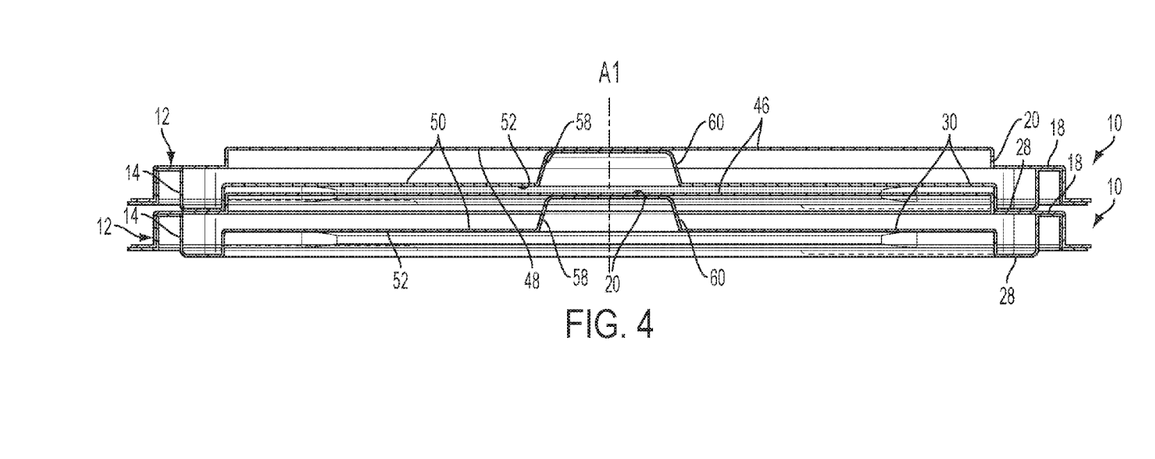
FIG. 4 is a front cross-sectional view of two stacked ostomy barrier ring packages according to an embodiment.

FIG. 4 illustrates an example of multiple packages 10 stacked together according to an embodiment of the present invention. Referring to FIGS. 3 and 4, the first diameter D1 of the plateau 46 is less than the second diameter D2 of the second recess 54. Accordingly, with multiple packages 10, the plateau 46 of one package 10 may be received or nested within the second recess 54 of another package 10 stacked thereon. That is, multiple packages 10, i.e., a system of packages, may be stacked and positively positioned relative to one another by way of the respective plateaus 46 being received in respective second recesses 54. As a result of the nesting configuration described above, a stack of multiple packages can be neatly and orderly stacked and stored and may resist toppling if bumped or otherwise disturbed. The difference between the first diameter D1 and the second diameter D2 may be sufficient to allow for easy positioning of the plateau 46 in the second recess 54, while leaving a clearance that is sufficiently small to limit relative motion of stacked packages 10 if the stack is bumped or otherwise disturbed.

In the stacked configuration, the second recess 54 of one package 10 may be in contact with and vertically supported by the plateau 46 of an adjacent stacked package 10. Alternatively, or in addition, the second exterior side 52 the one package 10 may be in contact with and supported by the first exterior side 44 of the adjacent stacked package 10.

The projection 60 may be generally centrally positioned in the package 10. The projection 60 may be generally circular in shape, to correspond to a central opening of a barrier ring, and extend along a first axis 'A1'. In one embodiment, the projection 60, the third recess 58, the pedestal 56, the second recess 54, the first recess 58 and the plateau 56 are concentrically positioned about the first axis 'A1'. Thus, each of the projection 60, the third recess 58, the pedestal 56, the second recess 54, the first recess 58 and the plateau 56 may be centrally, e.g., concentrically, positioned with respect to the package 10.

A cavity 62 is formed in the second shell 14 between the projection 60 and the second sidewall 32. The cavity 62 may extend further to an area defined between the pedestal 56 and the second sidewall 32. The cavity 62 is configured to receive the ostomy barrier ring 64 therein. The pedestal 56 is configured to support the ostomy barrier ring 64 thereon, and the projection 60 is configured to extend through the central opening of the ostomy barrier ring 64 (see FIG. 2) so as to positively position the ostomy barrier ring 64 within the package 10.

The package 10 is configured to receive an ostomy barrier ring 64 that is sized to rest substantially on the pedestal 56. That is, the package 10 is configured to receive an ostomy barrier ring 64 having a diameter that is substantially the same as a diameter of the pedestal 56. Accordingly, an outer periphery of the ostomy barrier ring 64 may be spaced from the second sidewall 32. Thus, the cavity 62, at an area between the ostomy barrier ring 64 and the second sidewall 32 generally defines a well surrounding the ostomy barrier ring 64 in which a user may manipulate or grasp an outer periphery of the ostomy barrier ring. As such, a user is not required to manipulate or grasp small release tabs on a liner of the ostomy barrier ring. In addition, with the ostomy barrier ring 64 positioned on the pedestal 56 as described above, perimeter sticking of the ostomy barrier ring 64 to the first shell 12 and/or second shell 14 of the package 10 may be reduced or eliminated.

In alternative embodiments where more than one second recess 54, and in turn, more than one corresponding pedestal 56 are provided, the pedestals 56 may, for example, be positioned about the projection 60, and the projection 60 may extend directly from the second interior side 50. In such an embodiment, the number of second recesses 54 may correspond to the number of plateaus 46 formed on the first exterior side 42. The plateaus 46 may be received in respective second recesses 54. As yet another alternative, a plurality of plateaus 46 may be provided. The plurality of plateaus 46 may extend into a single second recess 54 of an adjacently stacked package 10.

Figure 5:
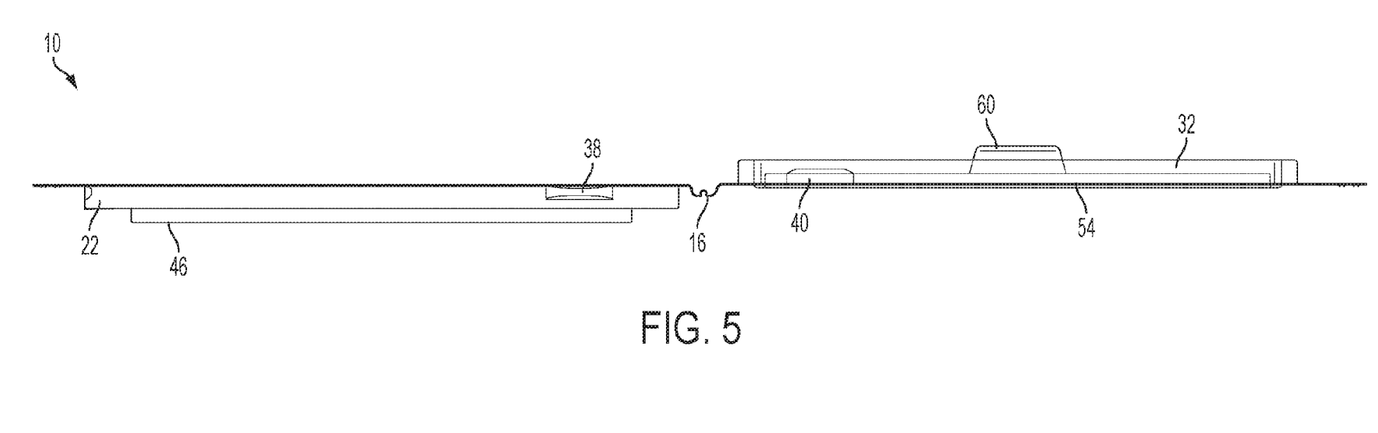
FIG. 5 is a is a side view of the ostomy barrier ring package in the open position.

FIG. 5 is a side view of the ostomy barrier ring package in the open position. Referring to FIG. 5, the hinge 16 may be a living hinge that is formed integrally with the first shell 12 and second 14. The hinge 16 may be formed with folds or bends so as to form a substantially "w" shape with the package 10 in the open position. The folds or bends may provide a flexible area at which the first shell 12 and second shell 14 may rotate relative to one another.

The package 10 may be made from a single, monolithic piece of material. For example, the package 10 may be made of a transparent plastic, or similar material, and may be formed by, for example, molding.

Figure 6:
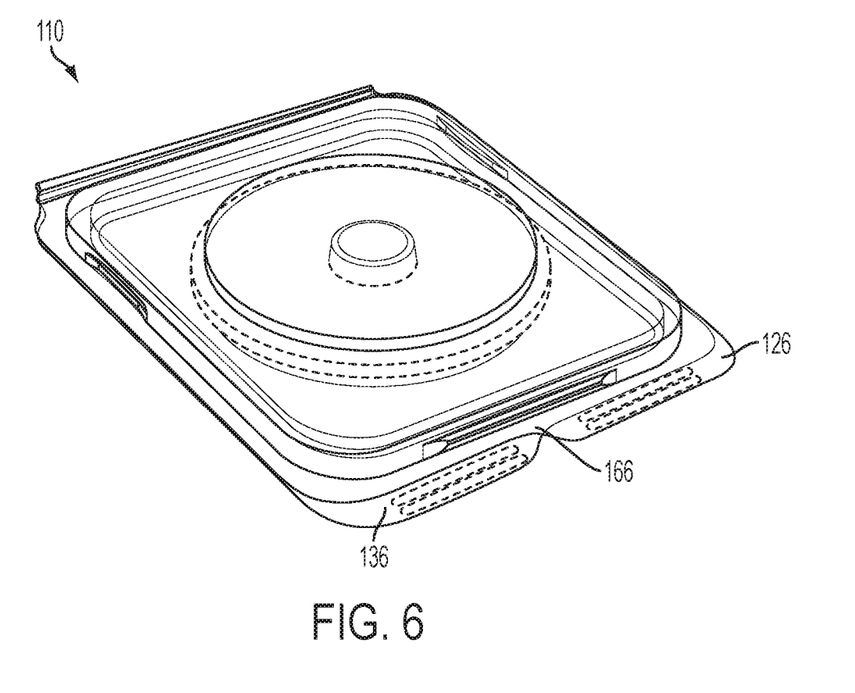
FIG. 6 is a perspective view of an ostomy barrier ring package according to another embodiment.

FIG. 6 is a perspective view of another package 110 for an ostomy barrier ring 64. It is understood that in the embodiments above, the dimensions of the package 10 may be determined before manufacture to accommodate ostomy barrier rings of varying sizes. For example, the packages 10 may be manufactured at different dimensions to accommodate a barrier ring having a diameter of approximately 2 inches and a barrier ring having a diameter of approximately 4 inches. While many of features described in the examples above may be adjusted, scaled or proportioned accordingly, the first opening tab 126 and second opening tab 136, for example, may be maintained at approximately the same dimensions between differently sized packages. As a result, and as shown in FIG. 6, a portion 166 of the first opening tab 126 may overlap a portion of the second opening tab 136. It is understood that features not expressly identified in the description of the package 110 in FIG. 6 may be similar to features described above with reference to FIGS. 1-5 and may be dimensioned similarly or proportioned to correspond to a size of the package 10.

The package 10 may be formed in any suitable shape that may accommodate a barrier ring 64 as described above while retaining the characteristics described above. For example, as shown in FIGS. 1, 2 and 6, the package may be generally square or rectangular shaped and include rounded corners. The hinge 16 may be formed generally along one side of the package 10. Alternatively, package 10 may be formed substantially as a circular or other suitable shape, with the hinge 16 positioned about at a portion of the periphery of the package 10.

It should also be understood that various changes and modifications to the presently disclosed embodiments will be apparent to those skilled in the art. Such changes and modifications can be made without departing from the spirit and scope of the present disclosure and without diminishing its intended advantages. It is therefore intended that such changes and modifications be covered by the appended claims.

The invention claimed is:

1. A package for an ostomy barrier ring comprising:
a first shell having a first stacking wall having a first interior side and a first exterior side, a first nesting structure formed on the first stacking wall, and a first sidewall extending downward from and about a periphery of the first stacking wall;
a second shell having a second stacking wall having a second interior side and a second exterior side, a second nesting structure formed on the second stacking wall, and a second sidewall extending upward from and about a periphery of the second stacking wall; and
a hinge connected to the first shell and second shell allowing the first shell and second shell to rotate relative to one another between an open position and closed position,
wherein the second nesting structure is a second recess formed in the second exterior side of the second stacking wall having an upwardly extending inner sidewall disposed radially inward of the second sidewall and a second nesting surface extending across an upper end of the inner sidewall on the second exterior side,
wherein the second recess defines a corresponding pedestal extending from the second stacking wall on the second interior side, the pedestal spaced from and disposed inwardly of the second sidewall by a cavity, and
wherein a third recess is formed radially within the second recess at the second exterior side, the third recess defining a corresponding projection extending from the pedestal at the second interior side.

2. The package of claim 1, wherein the first nesting structure is a plateau extending outwardly from the first exterior side.

3. The package of claim 2, wherein the plateau defines a corresponding first recess on the first interior side.

4. The package of claim 2, wherein the plateau has a first diameter and the second recess has a second diameter, wherein the second diameter is greater than the first diameter.

5. The package of claim 1, wherein the projection extends into the first recess.

6. The package of claim 1, wherein the cavity further extends between the projection and the second sidewall, wherein the cavity is configured to receive the ostomy barrier ring on the pedestal, and the ostomy barrier ring is spaced from the second sidewall.

7. The package of claim 1, further comprising a first peripheral flange extending about a portion of the first sidewall, and a second peripheral flange extending about a portion of the second sidewall.

8. The package of claim 7, wherein the first peripheral flange includes a first opening tab extending therefrom, and the second peripheral flange includes a second opening tab extending therefrom.

9. The package of claim 8, wherein at least a portion of the first opening tab and the second opening tab overlap.

10. The package of claim 1, wherein one of the first sidewall and the second sidewall is positioned within the other of the first sidewall or second wall with the first shell and second shell in the closed position.

11. The package of claim 1, wherein one of the first sidewall and second sidewall includes at least one lug, and the other of the first sidewall and second sidewall includes at least one corresponding groove configured to receive a corresponding one of the at least one lug in an interference fit with the first shell and second shell in the closed position.

12. The package of claim 1, wherein the hinge is a living hinge integrally formed with the first shell and second shell.

13. The package of claim 12, wherein the hinge is substantially w-shaped in cross section with the first shell and second shell in the open position.

14. A plurality of packages for ostomy barrier rings, each package comprising:

a first shell having a first stacking wall having a first interior side and a first exterior side, a first nesting structure formed on the first stacking wall, and a first sidewall extending from and about the first stacking wall such that the first stacking wall extends inwardly from the first sidewall;

a second shell having a second stacking wall having a second interior side and a second exterior side, a second nesting structure formed on the second stacking wall, and a second sidewall extending upward from and about a periphery of the second stacking wall; and a hinge connected to the first shell and second shell allowing the first shell and second shell to rotate relative to one another between an open position and closed position, wherein the second nesting structure of one package of the plurality of packages is configured to receive the first nesting structure of another package of the plurality of packages, wherein the first nesting structure is a plateau extending outwardly from the first exterior side and the second nesting structure is a second recess formed in the second exterior side, the second recess being inwardly spaced from the second sidewall and a having an upward extending inner sidewall and a second nesting surface wall extending across an upper end of the inner sidewall on the second exterior side, and wherein a third recess is formed radially within the second recess at the second exterior side, the third recess defining a corresponding projection extending upward on the second interior side.

15. The plurality of packages of claim 14, wherein the second recess defines a corresponding pedestal on the second interior side.

16. The plurality of packages of claim 15, wherein the projection extends into a first recess defined by the plateau at the first interior side.

* * * * *